(12) United States Patent
Garlock et al.

(10) Patent No.: US 11,000,319 B2
(45) Date of Patent: *May 11, 2021

(54) ARTHRODESIS DEVICES FOR GENERATING AND APPLYING COMPRESSION WITHIN JOINTS

(71) Applicant: ARTHREX, INC., Naples, FL (US)

(72) Inventors: Adam Garlock, Bonita Springs, FL (US); William Michael Karnes, Naples, FL (US); Matthew Fonte, Concord, MA (US); Matthew Palmer, Cambridge, MA (US); Robert Devaney, Auburndale, MA (US); Alexander Delmonaco, Billerica, MA (US); Kaitlyn Nealon, Somerville, MA (US)

(73) Assignee: ARTHREX, INC., Naples, FL (US)

(*) Notice: Subject to any disclaimer, the term of this patent is extended or adjusted under 35 U.S.C. 154(b) by 57 days.

This patent is subject to a terminal disclaimer.

(21) Appl. No.: 16/424,746

(22) Filed: May 29, 2019

(65) Prior Publication Data

US 2019/0274742 A1 Sep. 12, 2019

Related U.S. Application Data

(63) Continuation of application No. 15/489,067, filed on Apr. 17, 2017, now Pat. No. 10,307,190.

(60) Provisional application No. 62/322,847, filed on Apr. 15, 2016, provisional application No. 62/412,021, filed on Oct. 24, 2016.

(51) Int. Cl.
*A61B 17/72* (2006.01)
*A61B 17/00* (2006.01)

(52) U.S. Cl.
CPC ...... *A61B 17/7291* (2013.01); *A61B 17/7225* (2013.01); *A61B 17/7241* (2013.01); *A61B 2017/00862* (2013.01); *A61B 2017/00867* (2013.01)

(58) Field of Classification Search
CPC ............................................. A61B 17/72–7291
See application file for complete search history.

(56) References Cited

U.S. PATENT DOCUMENTS

| 3,986,504 A | * | 10/1976 | Avila | A61B 17/7225 606/63 |
| 4,875,475 A | * | 10/1989 | Comte | A61B 17/7225 606/64 |

(Continued)

FOREIGN PATENT DOCUMENTS

| EP | 1550418 A1 | 7/2005 |
| FR | 2289155 A1 | 5/1976 |

(Continued)

OTHER PUBLICATIONS

International Preliminary Report on Patentability for PCT Application No. PCT/US2017/027910, dated Oct. 25, 2018.

(Continued)

*Primary Examiner* — Eduardo C Robert
*Assistant Examiner* — Michelle C Eckman
(74) *Attorney, Agent, or Firm* — Carlson, Gaskey & Olds

(57) ABSTRACT

Arthrodesis devices and arthrodesis procedures are disclosed herein. In an embodiment, an arthrodesis device includes a shape memory material connecting member attached to two points of fixation.

20 Claims, 17 Drawing Sheets

(56) References Cited

U.S. PATENT DOCUMENTS

| | | | | |
|---|---|---|---|---|
| 5,034,012 | A * | 7/1991 | Frigg | A61B 17/72 606/62 |
| 5,263,955 | A * | 11/1993 | Baumgart | A61B 17/7216 606/62 |
| 5,352,228 | A * | 10/1994 | Kummer | A61B 17/1721 606/64 |
| 5,505,734 | A * | 4/1996 | Caniggia | A61B 17/7225 606/63 |
| 6,648,890 | B2 | 11/2003 | Culbert et al. | |
| 6,786,908 | B2 * | 9/2004 | Hover | A61B 17/72 606/62 |
| 6,932,819 | B2 * | 8/2005 | Wahl | A61B 17/7225 606/67 |
| 7,410,488 | B2 * | 8/2008 | Janna | A61B 17/72 606/62 |
| 7,985,222 | B2 | 7/2011 | Gall et al. | |
| 8,118,952 | B2 | 2/2012 | Gall et al. | |
| 8,162,942 | B2 | 4/2012 | Coati et al. | |
| 8,439,916 | B2 | 5/2013 | Coati et al. | |
| 8,460,293 | B2 | 6/2013 | Coati et al. | |
| 8,491,583 | B2 | 7/2013 | Gall et al. | |
| 8,876,821 | B2 | 11/2014 | Kinmon | |
| 9,138,266 | B2 | 9/2015 | Stauch | |
| 9,308,031 | B2 * | 4/2016 | Elghazaly | A61B 17/7241 |
| 9,320,551 | B2 * | 4/2016 | Frank | A61B 17/7233 |
| 9,381,052 | B2 | 7/2016 | Ziran | |
| 9,445,850 | B2 | 9/2016 | Kinmon | |
| 9,770,274 | B2 * | 9/2017 | Pool | A61B 17/7216 |
| 9,931,146 | B2 * | 4/2018 | Gorsline | A61B 17/7291 |
| 2002/0055744 | A1 | 5/2002 | Reiley | |
| 2005/0216007 | A1 * | 9/2005 | Woll | A61B 17/7258 606/62 |
| 2006/0293683 | A1 * | 12/2006 | Stauch | A61B 17/7216 606/90 |
| 2007/0213725 | A1 * | 9/2007 | Hack | A61B 17/7225 606/62 |
| 2008/0221577 | A1 * | 9/2008 | Elghazaly | A61B 17/744 606/64 |
| 2010/0010490 | A1 * | 1/2010 | Brigido | A61B 17/1775 606/64 |
| 2010/0268285 | A1 * | 10/2010 | Tipirneni | A61B 17/744 606/309 |
| 2011/0004212 | A1 | 1/2011 | Gall et al. | |
| 2011/0054473 | A1 * | 3/2011 | Brigido | A61B 17/1725 606/62 |
| 2011/0230883 | A1 * | 9/2011 | Zahrly | A61B 17/7216 606/63 |
| 2012/0130370 | A1 * | 5/2012 | Kinmon | A61B 17/7225 606/62 |
| 2012/0136356 | A1 * | 5/2012 | Doherty | A61B 17/7225 606/62 |
| 2012/0209265 | A1 * | 8/2012 | Pool | A61F 2/28 606/55 |
| 2012/0209268 | A1 * | 8/2012 | Overes | A61B 17/7225 606/62 |
| 2012/0239038 | A1 * | 9/2012 | Saravia | A61B 17/7208 606/64 |
| 2013/0012942 | A1 * | 1/2013 | Nelson | A61B 17/7266 606/63 |
| 2013/0085502 | A1 * | 4/2013 | Harrold | A61B 17/7225 606/96 |
| 2013/0116693 | A1 * | 5/2013 | Nelson | A61B 17/1725 606/64 |
| 2013/0325010 | A1 * | 12/2013 | Prien | A61B 17/725 606/64 |
| 2014/0005669 | A1 * | 1/2014 | Graham | A61B 17/7233 606/62 |
| 2014/0114311 | A1 * | 4/2014 | Pool | A61B 17/7216 606/62 |
| 2014/0142575 | A1 | 5/2014 | Biedermann et al. | |
| 2014/0228845 | A1 * | 8/2014 | Gorsline | A61B 17/8869 606/62 |
| 2016/0058483 | A1 * | 3/2016 | Stauch | A61B 17/7216 606/63 |
| 2016/0199109 | A1 * | 7/2016 | Zehtab | A61B 17/7233 606/64 |
| 2017/0100163 | A1 * | 4/2017 | Palmer | A61B 17/808 |
| 2017/0172624 | A1 * | 6/2017 | Brunner | A61B 17/7016 |
| 2017/0296241 | A1 * | 10/2017 | Garlock | A61B 17/7291 |
| 2018/0092677 | A1 * | 4/2018 | Peterson | A61B 17/7225 |

FOREIGN PATENT DOCUMENTS

| | | |
|---|---|---|
| WO | 2009/108194 A1 | 9/2009 |
| WO | 2011/008739 A2 | 1/2011 |

OTHER PUBLICATIONS

International Search Report and Written Opinion of the International Searching Authority for International Application No. PCT/US2017/027910 dated Sep. 6, 2017.

International Search Report and Written Opinion of the International Searching Authority for International application No. PCT/US2019/040783 dated Sep. 24, 2019.

* cited by examiner

Before Dynamic Compression

Dynamic Compression

ARTHRODESIS DEVICES FOR GENERATING AND APPLYING COMPRESSION WITHIN JOINTS

CROSS-REFERENCE TO RELATED APPLICATIONS

This is a continuation of U.S. patent application Ser. No. 15/489,067, filed Apr. 17, 2017, which claims priority to U.S. Provisional Application No. 62/322,847, filed on Apr. 15, 2016, and further claims priority to U.S. Provisional Application No. 62/412,021, filed on Oct. 24, 2016.

The entire disclosures of each of the above priority applications are incorporated herein by reference.

BACKGROUND

This disclosure relates to intramedullary devices, and more particularly to arthrodesis (i.e., fusion) devices for generating and applying compression within a joint.

Arthrodesis procedures are common in the field of orthopedic surgery for repairing arthritic and deteriorated bones. The success of these surgical procedures often depends on the successful approximation of bone and on the amount of compression achieved between the bones.

Intramedullary devices can be used during arthrodesis procedures. These devices are designed to reduce and create a compressive load between bones. However, known intramedullary devices do not always achieve this goal. It would therefore be useful if intramedullary devices were available that generate and maintain a compressive load within a joint while bone healing occurs.

SUMMARY

This disclosure relates to arthrodesis devices, such as intramedullary nails, for performing arthrodesis or fusion procedures within human or animal bodies.

The arthrodesis devices described herein may be capable of bringing bones or bone fragments in proximity to one another, generating a compressive load, and maintaining the compressive load for a prolonged period of time while healing occurs.

An arthrodesis device includes, inter alia, a nail body extending along a longitudinal axis between a proximal portion and a distal portion. A proximal slider is housed inside the proximal portion, and a distal slider is housed inside the distal portion. A shape memory material rod is connected to both the proximal slider and the distal slider. A cable is connected to the distal slide. The cable may be tensioned to move the distal slider inside the nail body and thereby stretch the shape memory material rod.

Another arthrodesis device includes, inter alia, a nail body extending along a longitudinal axis between a proximal portion and a distal portion, a proximal interlocking fixation body located inside or outside the proximal portion, a distal interlocking fixation body located inside or outside the distal portion, and a shape memory material connecting member attached to the proximal interlocking fixation body and the distal interlocking fixation body.

A method for performing an arthrodesis procedure includes, inter alia, inserting an arthrodesis device within a joint, inserting a first fixation device through the arthrodesis device, inserting a second fixation device through the arthrodesis device, tensioning a cable of the arthrodesis device such that the cable alters a shape memory material connecting member of the arthrodesis device from an unstretched condition to a stretched condition, and releasing tension on the cable. Releasing tension on the cable causes the shape memory material connecting member to move back toward the unstretched condition, thereby applying a compressive load across bones of the joint.

DETAILED DESCRIPTION

Figure 1:
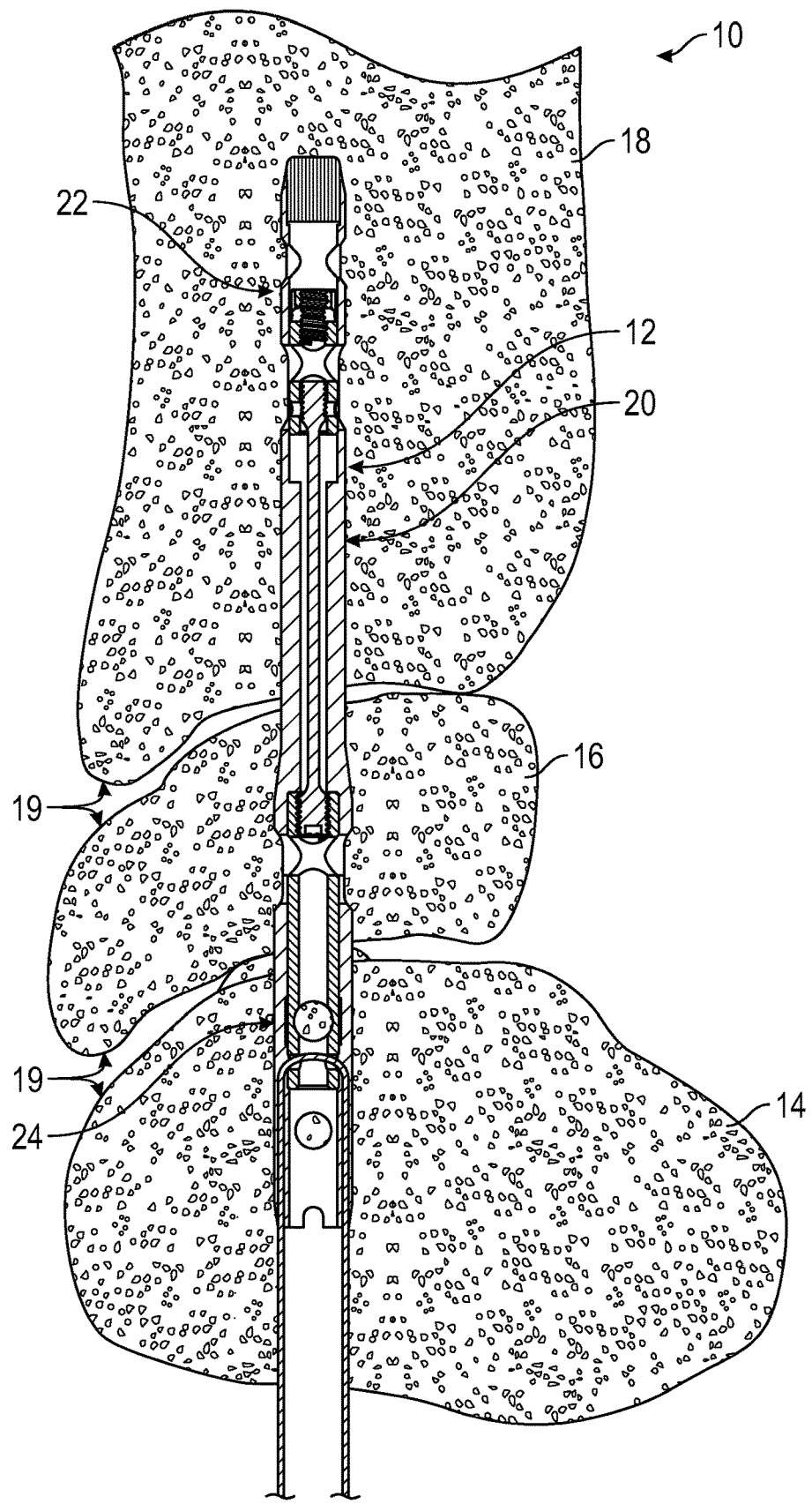
FIG. 1 illustrates a joint of the human musculoskeletal system.
Figure 2:
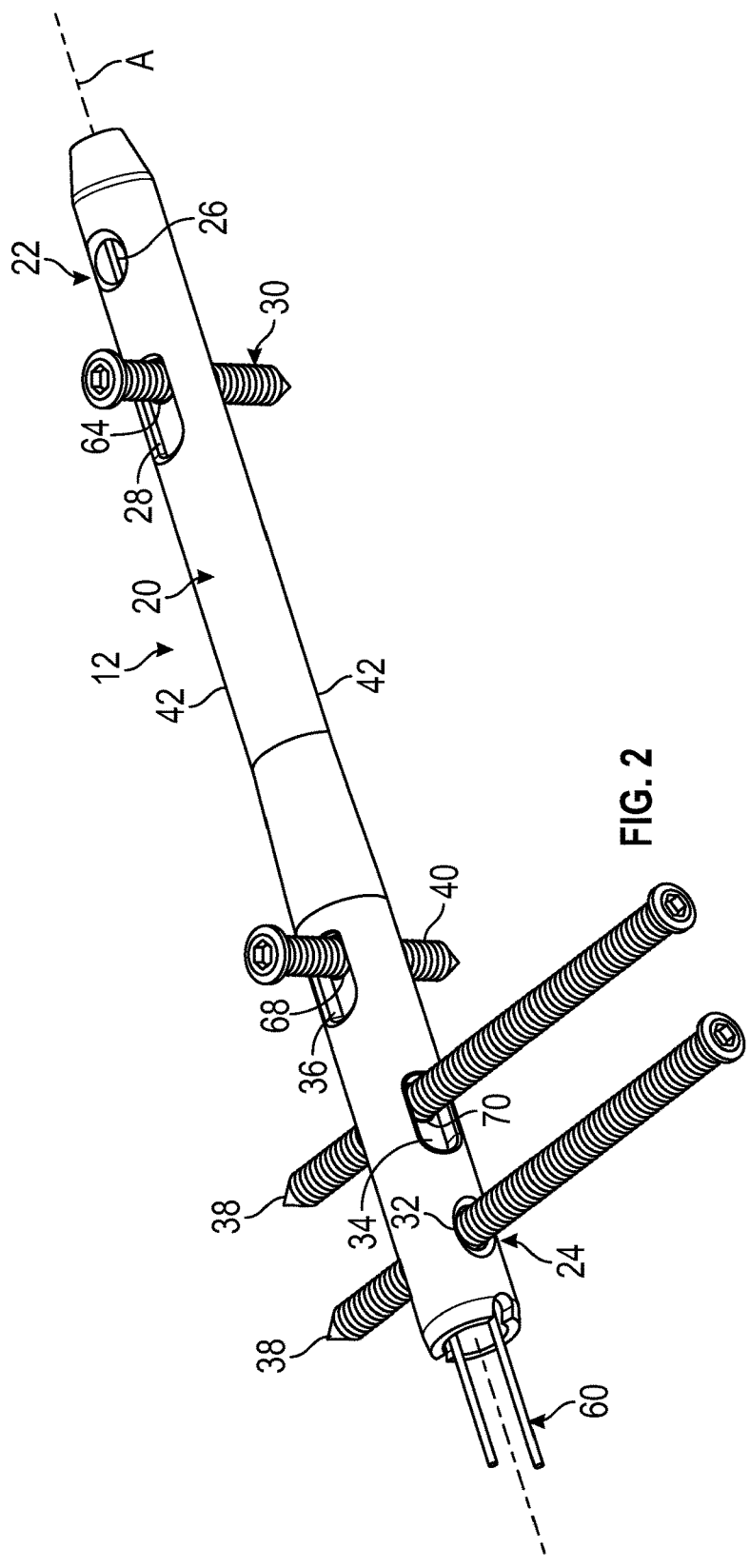
FIG. 2 illustrates an arthrodesis device for performing arthrodesis procedures.
Figure 3:
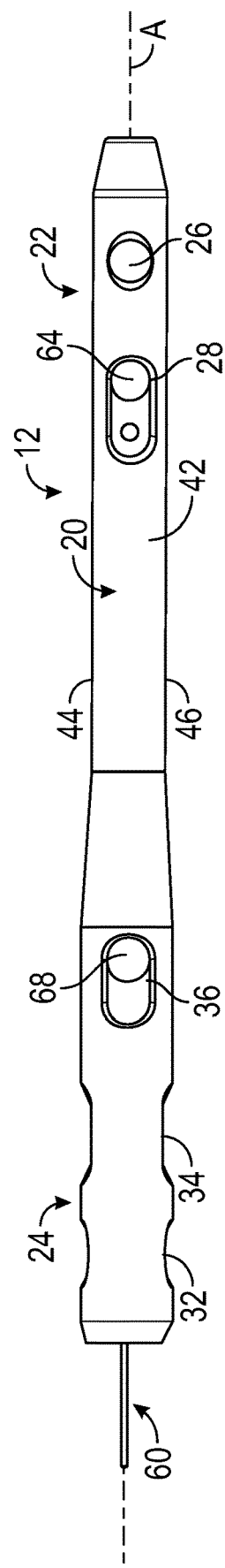
FIG. 3 is a front view of the arthrodesis device of FIG. 2.
Figure 4:
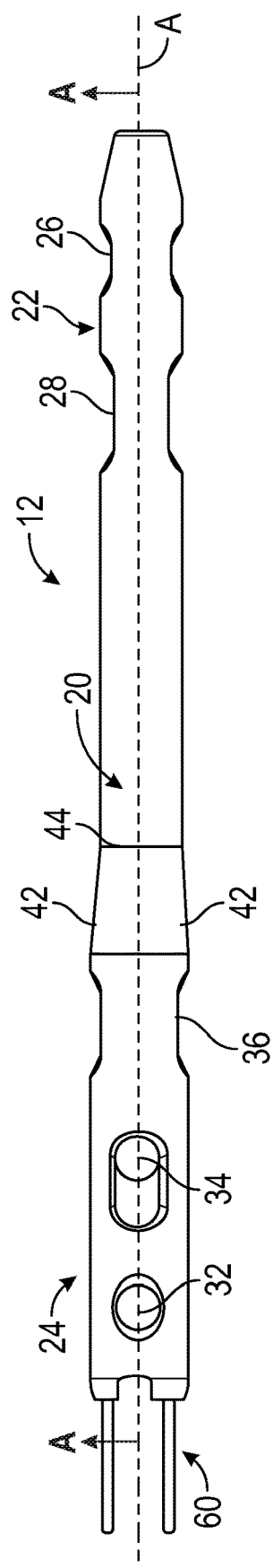
FIG. 4 is a top view of the arthrodesis device of FIG. 2.

This disclosure describes exemplary arthrodesis devices, such as intramedullary nails, for performing arthrodesis or fusion procedures within human or animal bodies. The arthrodesis devices described by this disclosure are capable of bringing bones or bone fragments in proximity to one another, generating a compressive load, and maintaining the compressive load for a prolonged period of time while healing occurs.

An arthrodesis device includes, inter alia, a nail body extending along a longitudinal axis between a proximal portion and a distal portion. A proximal slider is housed inside the proximal portion, and a distal slider is housed inside the distal portion. A shape memory material rod is connected to both the proximal slider and the distal slider. A cable is connected to the distal slide. The cable may be tensioned to move the distal slider inside the nail body and thereby stretch the shape memory material rod.

Another arthrodesis device includes, inter alia, a nail body extending along a longitudinal axis between a proximal portion and a distal portion, a proximal interlocking fixation body located inside or outside the proximal portion, a distal interlocking fixation body located inside or outside the distal portion, and a shape memory material connecting member attached to the proximal interlocking fixation body and the distal interlocking fixation body.

In a further embodiment, a nail body of an arthrodesis device includes at least one opening configured to receive a fixation device, such as a screw, peg, etc.

In a further embodiment, a proximal interlocking fixation body is located inside a proximal portion of a nail body and a distal interlocking fixation body is located inside a distal portion of the nail body.

In a further embodiment, a proximal interlocking fixation body is located outside a proximal portion of a nail body and a distal interlocking fixation body is located outside a distal portion of the nail body In a further embodiment, a first opening of a nail body of an arthrodesis device is located within a proximal portion of the nail body and receives a tibial screw, a second opening is located within a distal portion of the nail body and receives a talar screw, and a third opening is located within the distal portion of the nail body and receives a calcaneal screw.

In a further embodiment, a shape memory material connecting member of an arthrodesis device is a rod made of Nitinol (NiTi).

In a further embodiment, a shape memory material connecting member of an arthrodesis device includes an elongated shaft extending between a first threaded portion and a second threaded portion.

In a further embodiment, a first threaded portion of a shape memory material connecting member of an arthrodesis device is received within a first threaded opening of a proximal interlocking fixation body, and a second threaded portion is received within a second threaded opening of a distal interlocking fixation body. Thereby, a shape memory material connecting member (e.g., nitinol) is attached to at least two points of fixation (e.g., fixation devices received through proximal and distal interlocking fixation bodies).

In a further embodiment, a distal interlocking fixation body of an arthrodesis device is translatable within a cannulation of a nail body.

In a further embodiment, a cable of an arthrodesis device is connected to a distal interlocking fixation body. The cable is tensioned to move the distal interlocking fixation body inside a nail body.

In a further embodiment, when a nail body of an arthrodesis device is implanted, a shape memory material connecting member is movable between an unstretched position and a stretched position to generate a compressive force across bones of a joint.

A method for performing an arthrodesis procedure includes, inter alia, inserting an arthrodesis device within a joint, inserting a first fixation device through the arthrodesis device, inserting a second fixation device through the arthrodesis device, tensioning a cable of the arthrodesis device such that the cable alters a shape memory material connecting member of the arthrodesis device from an unstretched condition to a stretched condition, and releasing tension on the cable. Releasing tension on the cable causes the shape memory material connecting member to move back toward the unstretched condition, thereby applying a compressive load across bones of the joint.

In a further embodiment, a joint that is repaired during an arthrodesis procedure is a tibio-talo-calcaneal (TTC) joint of an ankle.

In a further embodiment, a method includes, prior to inserting an arthrodesis device, inserting a guide wire into a joint, and reaming a passage through the joint for accommodating the arthrodesis device.

In a further embodiment, a first fixation device is a most distal calcaneal screw tibial screw and a second fixation device is a tibial screw through a proximal interlocking fixation body.

In a further embodiment, a method includes inserting a third fixation device through an arthrodesis device after inserting a second fixation device. The third fixation device is either a talar screw or a calcaneal screw.

In a further embodiment, a shape memory material connecting member connects between a proximal interlocking fixation body and a distal interlocking fixation body of an arthrodesis device and a cable is connected to the distal interlocking fixation body. The cable is tensioned to translate the distal interlocking fixation body in a proximal to distal direction.

In a further embodiment, translating a distal interlocking fixation body moves a shape memory material connecting member of an arthrodesis device from an unstretched condition to a stretched condition.

In a further embodiment, a proximal interlocking fixation body is fixed from movement prior to tensioning a cable.

In a further embodiment, inserting a third fixation device substantially locks a positioning of a distal interlocking fixation body of an arthrodesis device.

In a further embodiment, a third fixation device is a calcaneal screw.

FIG. 1 schematically illustrates a joint 10 of the human musculoskeletal system that has been repaired using an arthrodesis device 12. In an embodiment, the arthrodesis device 12 is specifically configured for use with a tibio-talo-calcaneal (TTC) joint of an ankle. However, the arthrodesis devices 12 of this disclosure could be used to repair other joints within the scope of this disclosure (e.g., femoral, humeral, tibial, etc.).

The joint 10 includes a calcaneus 14, a talus 16, and a tibia 18. The joint 10 may become unstable if there is significant cartilage loss and/or diseased bone at the articulating surfaces 19 of the calcaneus 14, the talus 16, and/or the tibia 18. Over time, the patient suffering from this instability can develop arthritis, thus resulting in significant pain.

This disclosure describes arthrodesis devices for fusing such unstable joints. Fusing the bones of the joint 10 together causes the calcaneus 14, the talus 16, and the tibia 18 to act as a single bone, thus substantially eliminating motion and reducing pain caused by the arthritic joint. Although TTC joint fusions of the ankle are described throughout this disclosure as one example arthrodesis technique, this disclosure is not intended to be limited to only TTC joint fusions.

FIGS. 2, 3, 4, and 5 illustrate an exemplary arthrodesis device 12 according to a first embodiment of this disclosure. The arthrodesis device 12 includes a nail body 20 that extends along a longitudinal axis A between a proximal portion 22 and a distal portion 24. In an embodiment, the arthrodesis device 12 is configured such that once the arthrodesis device 12 has been implanted within the joint 10 of FIG. 1, the proximal portion 22 of the nail body 20 extends into the tibia 18 of the joint 10, and the distal portion 24 of the nail body 20 extends into both the calcaneus 14 and the talus 16 of the joint 10 (see, e.g., FIG. 1).

The nail body 20 is configured as a sleeve for housing other components of the arthrodesis device 12 (discussed further below). In an embodiment, the nail body 20 may be made of a titanium alloy, such as Ti-6Al-4V. However, other materials are also contemplated within the scope of this disclosure.

The nail body 20 includes multiple openings for receiving fixation devices, such as screws, pegs, etc., for fixating the arthrodesis device 12 within the joint 10. For example, the proximal portion 22 of the nail body 20 may include a first proximal opening 26 and a second proximal opening 28 that is slightly distal (i.e., displaced in a direction toward the distal portion 24) to the first proximal opening 26. Each of the first proximal opening 26 and the second proximal opening 28 may receive a tibial screw 30 for fixating the arthrodesis device 12 to the tibia 18. In an embodiment, the first proximal opening 26 is a round opening and the second proximal opening 28 is an elongated slot. In another embodiment, the first proximal opening 26 and the second proximal opening 28 extend through opposing side surfaces 42 of the nail body 20, which may extend at a perpendicular angle relative to the longitudinal axis A (see, e.g., FIG. 2 and side view of FIG. 3).

The distal portion 24 of the nail body 20 may include a first distal opening 32, a second distal opening 34, and a third distal opening 36. The second distal opening 34 may be just proximal of the first distal opening 32 (i.e., displaced in a direction toward the proximal portion 22), and the third distal opening 36 may be just proximal to the second distal opening 34. The first and second distal openings 32, 34 may each receive a calcaneal screw 38 for fixating the arthrodesis device 12 to the calcaneus 14, and the third distal opening 36 may receive a talar screw 40 for fixating the arthrodesis device 12 to the talus 16. In an embodiment, the first distal opening 32 is a round opening and the second and third distal openings 34, 36 are elongated slots. In another embodiment, the first and second distal openings 32, 34 extend through a top surface 44 and a bottom surface 46 of the nail body 20, and may extend at a perpendicular angle relative to the longitudinal axis A (see, e.g., FIG. 2 and top view of FIG. 4). The third distal opening 36 extends through the opposing side surface 42 of the nail body 20, and may extend at a perpendicular angle relative to the longitudinal axis A (see, e.g., FIG. 2 and top view of FIG. 4). The first proximal opening 26, the second proximal opening 28, and the third distal opening 36 may therefore extend in parallel with one another. Further, the first and second distal openings 32, 34 may extend perpendicular to the first proximal opening 26, the second proximal opening 28, and the third distal opening 36.

Figure 5:
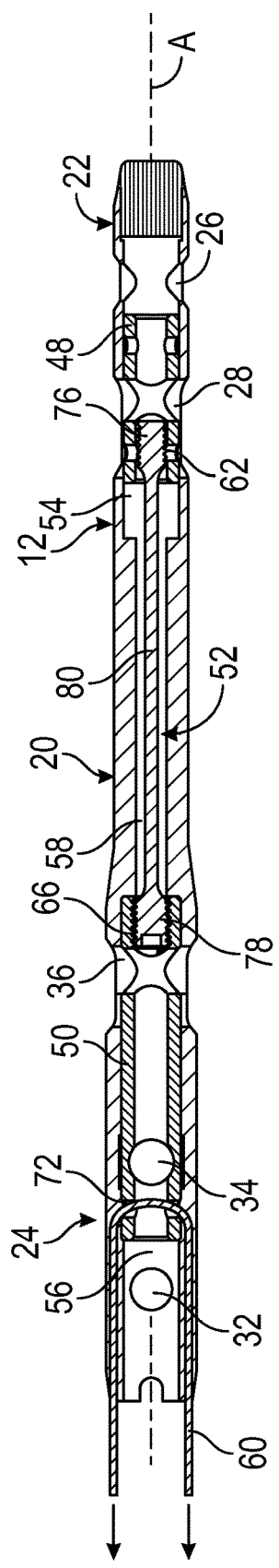
FIG. 5 is a cross-sectional view taken through section A-A of FIG. 4.

As best illustrated by the cross-sectional view of FIG. 5, the nail body 20 of the arthrodesis device 12 may house a proximal interlocking fixation body 48, a distal interlocking fixation body 50, and a shape memory material connecting member 52. The proximal interlocking fixation body 48 is slidably received within a first cannulation 54 of the nail body 20 and is at least partially exposed within the second proximal opening 28, the distal interlocking fixation body 50 is slidably received within a second cannulation 56 of the nail body 20 and is at least partially exposed within the second and third distal openings 34, 36, and the shape memory material connecting member 52 is received within a third cannulation 58 of the nail body 20 and is connected (e.g., threadably engaged) to both the proximal interlocking fixation body 48 and the distal interlocking fixation body 50. In an embodiment, the proximal interlocking fixation body 48 and the distal interlocking fixation body 50 act as sliders that move inside the nail body 20.

In an embodiment, the proximal interlocking fixation body 48 and the distal interlocking fixation body 50 are made of a titanium alloy, such as Ti-6Al-4V. In another embodiment, the proximal interlocking fixation body 48 and the distal interlocking fixation body 50 are proximal and distal sliders, respectively, of the arthrodesis device 12.

In another embodiment, the shape memory material connecting member 52 may be configured as a rod, e.g., a rod made of Nitinol (NiTi). However, the shape memory material connecting member 52 could have other shapes and configurations, and other superelastic materials (e.g., materials capable of exhibiting superelasticity and/or a temperature-induced shape changes) can be used to construct the shape memory material connecting member 52.

The arthrodesis device 12 additionally includes a cable 60, which may be used as a tensioning device as will be described. The cable 60 is attached to the distal interlocking fixation body 50 and extends to a location outside of the nail body 20. In an embodiment, the cable 60 is made of stainless steel, such as 304V Stainless Steel.

In use, the cable 60 may be tensioned to move the distal interlocking fixation body 50 within the second cannulation 56, thereby stretching the shape memory material connecting member 52 to a stretched position. Once stretched, the superelasticity of the shape memory material connecting member 52 causes it to want to return toward its unstretched position. The arthrodesis device 12 can therefore apply a constant compression force across the bones of the joint 10 once fixated within the joint 10.

Figure 6A:
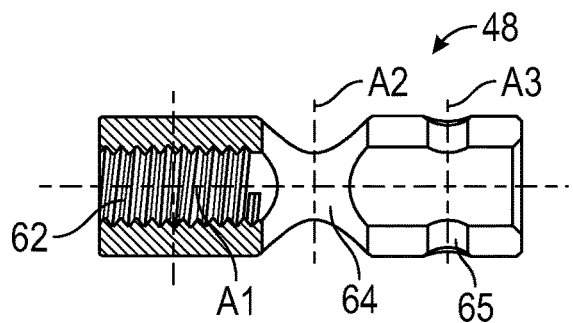
FIG. 6A illustrates a proximal interlocking fixation body of the arthrodesis device of FIG. 2.
Figure 6B:
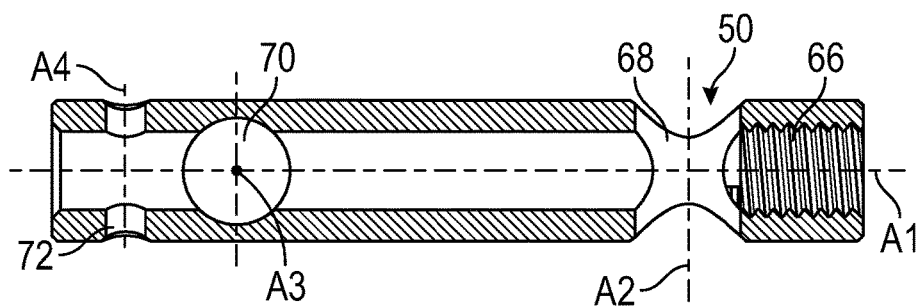
FIG. 6B illustrates a distal interlocking fixation body of the arthrodesis device of FIG. 2.

FIGS. 6A and 6B illustrate additional features of the proximal interlocking fixation body 48 and the distal interlocking fixation body 50, respectively. Referring first to FIG. 6A, the proximal interlocking fixation body 48 includes a threaded opening 62 extending along a first axis A1 and a non-threaded opening 64 extending along a second axis A2. In an embodiment, the second axis A2 is perpendicular to the first axis A1. The threaded opening 62 may receive a portion of the shape memory material connecting member 52 (see FIG. 5), and the non-threaded opening 64 may receive a tibial screw 30 (see FIG. 2). A second non-threaded opening 65 may extend along a third axis A3 that is parallel to the second axis A2. The second non-threaded opening 65 may receive a pin, such as a PLLA pin, that can be press fit into place so the proximal interlocking fixation body 48 does not move before tensioning the cable 60.

Referring now to FIG. 6B, the distal interlocking fixation body 50 includes a threaded opening 66 extending along a first axis A1, a first non-threaded opening 68 extending along a second axis A2, a second non-threaded opening 70 extending along a third axis A3, and a third non-threaded opening 72 extending along a fourth axis A4. In an embodiment, the second axis A2, the third axis A3, and the fourth axis A4 are each perpendicular to the first axis A1. In another embodiment, the second and fourth axes A2, A4 are parallel to one another but perpendicular to the third axis A3. The threaded opening 66 may receive a portion of the shape memory material connecting member 52 (see FIG. 5), the first non-threaded opening 68 may receive a talar screw 40 that extends through the third distal opening 36 of the nail body 20 (see FIG. 2), the second non-threaded opening 70 may receive a calcaneal screw 38 that extends through the second distal opening 34 of the nail body 20 (see FIG. 2), and the third non-threaded opening 70 may receive the cable 60 of the arthrodesis device 12 (see FIG. 5).

Figure 7:
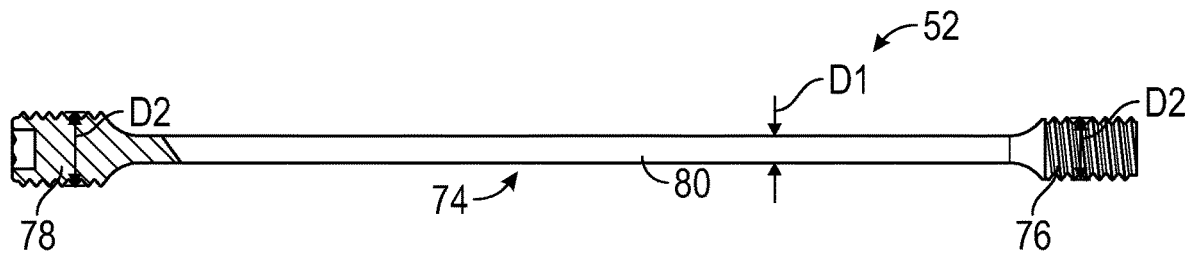
FIG. 7 illustrates a shape memory material connecting member of the arthrodesis device of FIG. 2.

FIG. 7 illustrates additional features of the shape memory material connecting member 52. The shape memory material connecting member 52 may include an elongated body 74 having a first threaded portion 76, a second threaded portion 78, and a shaft 80 extending between the first threaded portion 76 and the second threaded portion 78. In an embodiment, the first threaded portion 76 and the second threaded portion 78 include a second diameter D2 that is larger than a first diameter D1 of the shaft 80. The first threaded portion 76 may engage the threaded opening 62 of the proximal interlocking fixation body 48 and the second threaded portion 78 may engage the threaded opening 66 of the distal interlocking fixation body 50 to connect the shape memory material connecting member 52 to each of the proximal and distal interlocking fixation bodies 48, 50 (see FIG. 5). The shaft 80 may be disposed within the third cannulation 58 of the nail body 20.

Figure 8:
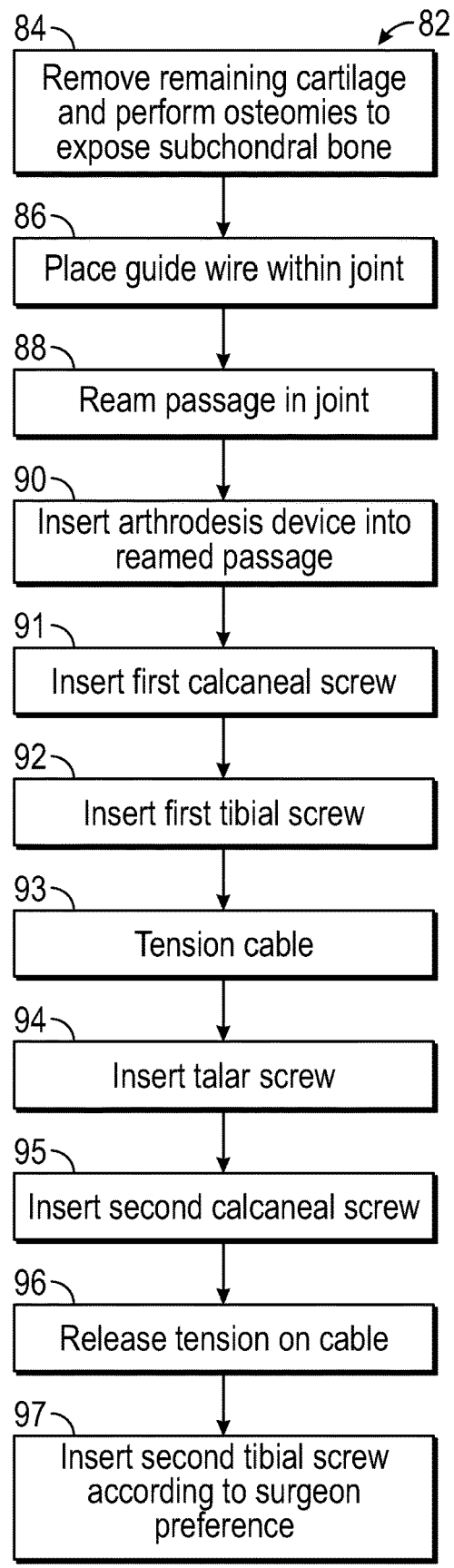
FIG. 8 schematically illustrates an exemplary method for performing an arthrodesis procedure.

FIG. 8, with continued reference to FIGS. 1-7, schematically illustrates a method 82 for performing an arthrodesis procedure. The method 82 is described for using the arthrodesis device 12 to fuse together the bones of the joint 10 shown in FIG. 1. However, other joints could be repaired using a similar procedure as the one described below. It should be appreciated that features of the arthrodesis device 12 may be specifically configured in order to provide the method 82 described. It should further be understood that the method 82 described could include a greater or fewer number of steps and that the steps could be performed in a different order within the scope of this disclosure.

The method 82 begins at block 84 by removing any remaining cartilage and performing any necessary osteotomies to remove diseased bone and expose the subchondral bone of the calcaneus 14, the talus 16, and the tibia 18. This step creates the necessary surface areas for fusing the calcaneus 14, the talus 16, and the tibia 18 together.

Next, as schematically illustrated at block 86, a guide wire is placed so it extends through the calcaneus 14 and the talus 16 and extends partially into the tibia 18. The guide wire is drilled into the joint 10 in an inferior-to-superior direction (i.e., entering through inferior side of calcaneus 14, and then through talus 16 and into tibia 18). A passage is then reamed into the joint 10 at block 88 for accommodating the arthrodesis device 12. A reamer may be inserted over the guide wire to ream the passage.

The arthrodesis device 12 is inserted into the reamed passage at block 90. Placement of the arthrodesis device 12 may be guided by a targeting device (not shown). Insertion of the arthrodesis device 12 may require light tapping to insert the arthrodesis device 12 at the proper distance within the tibia 18.

A calcaneal screw 38 is inserted through the first distal opening 32 of the nail body 20 at block 91 to affix the arthrodesis device 12 in place. Then, at block 92, a tibial screw 30 is inserted through the second proximal opening 28 of the nail body 20 and through the non-threaded opening 64 of the proximal interlocking fixation body 48. Insertion of the tibial screw 30 in this manner substantially locks the proximal interlocking fixation body 48 from further movement relative to the nail body 20.

The cable 60 is tensioned at block 93. The cable 60 may be tensioned using a suitable tensioning device (not shown). Tensioning the cable 60 moves (e.g., slides) the distal interlocking fixation body 50 distally within the third distal opening 36. The distal interlocking fixation body 50 may therefore operate as a slider inside the nail body 20. Since the proximal interlocking fixation body 48 is now fixed, this movement stretches the shape memory material connecting member 52 to generate a compressive load. The tension is held on the cable 60 while a talar screw 40 is inserted through the third distal opening 36 of the nail body 20 and through the first non-threaded opening 68 of the distal interlocking fixation body 50 at block 94. A second calcaneal screw 38 is inserted through the second distal opening 34 of the nail body 20 and through the second non-threaded opening 70 of the distal interlocking fixation body 50 at block 95.

Tension may then be released from the cable 60 at block 96. The cable 60 is then removed. Releasing the tension on the cable 60 causes the shape memory material connecting member 52 to attempt to recover the strain caused by stretching the shape memory material connecting member 52 to the stretched position, thus creating and maintaining a compressive force across the bones of the joint 10.

The method 82 may conclude at block 97 by inserting a second tibial screw 30 through the first proximal opening 26 of the nail body 20. This step may optionally be performed and is based on the surgeon's discretion.

Figure 9:
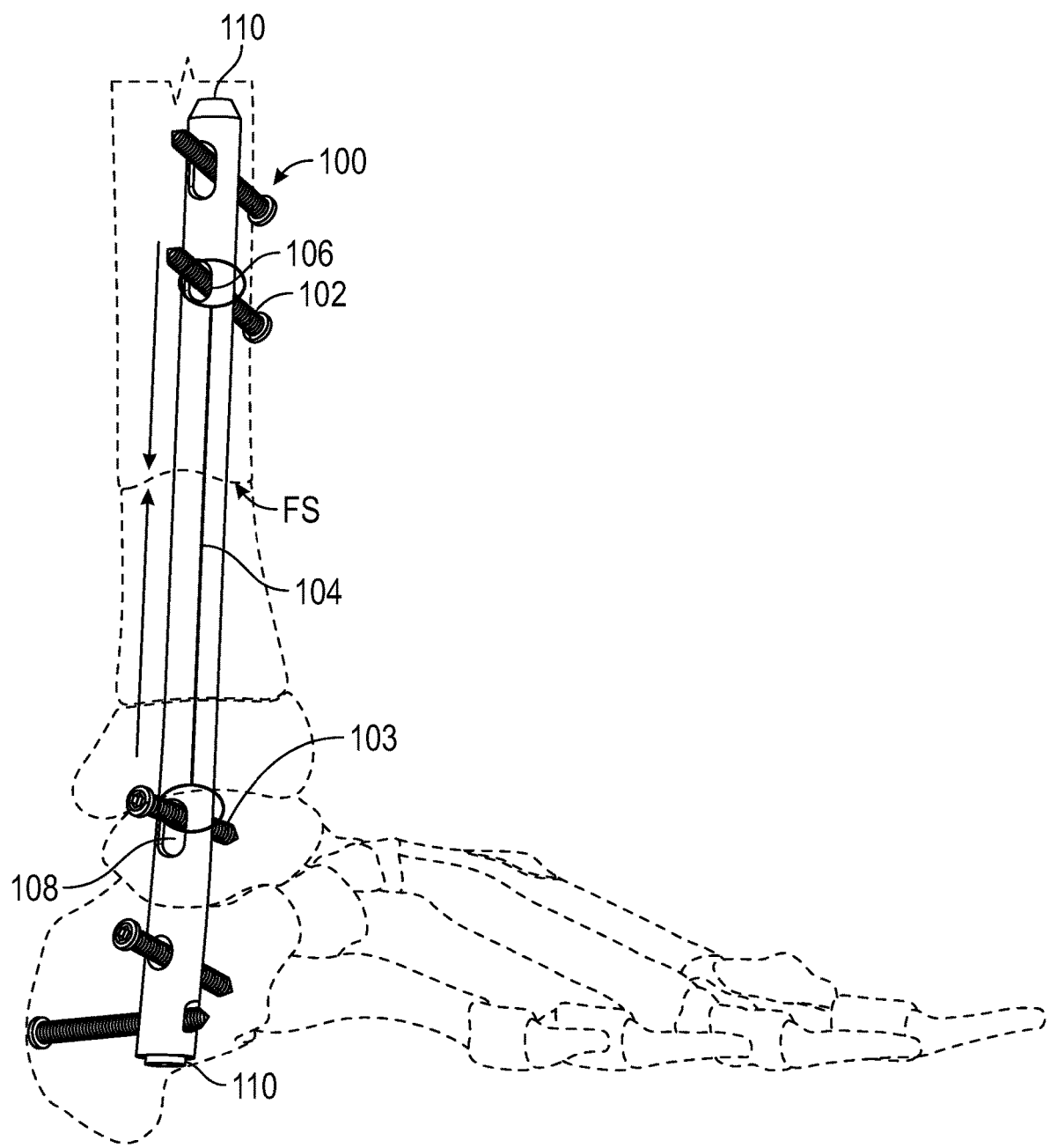
FIG. 9 illustrates another exemplary arthrodesis device.
Figure 10:
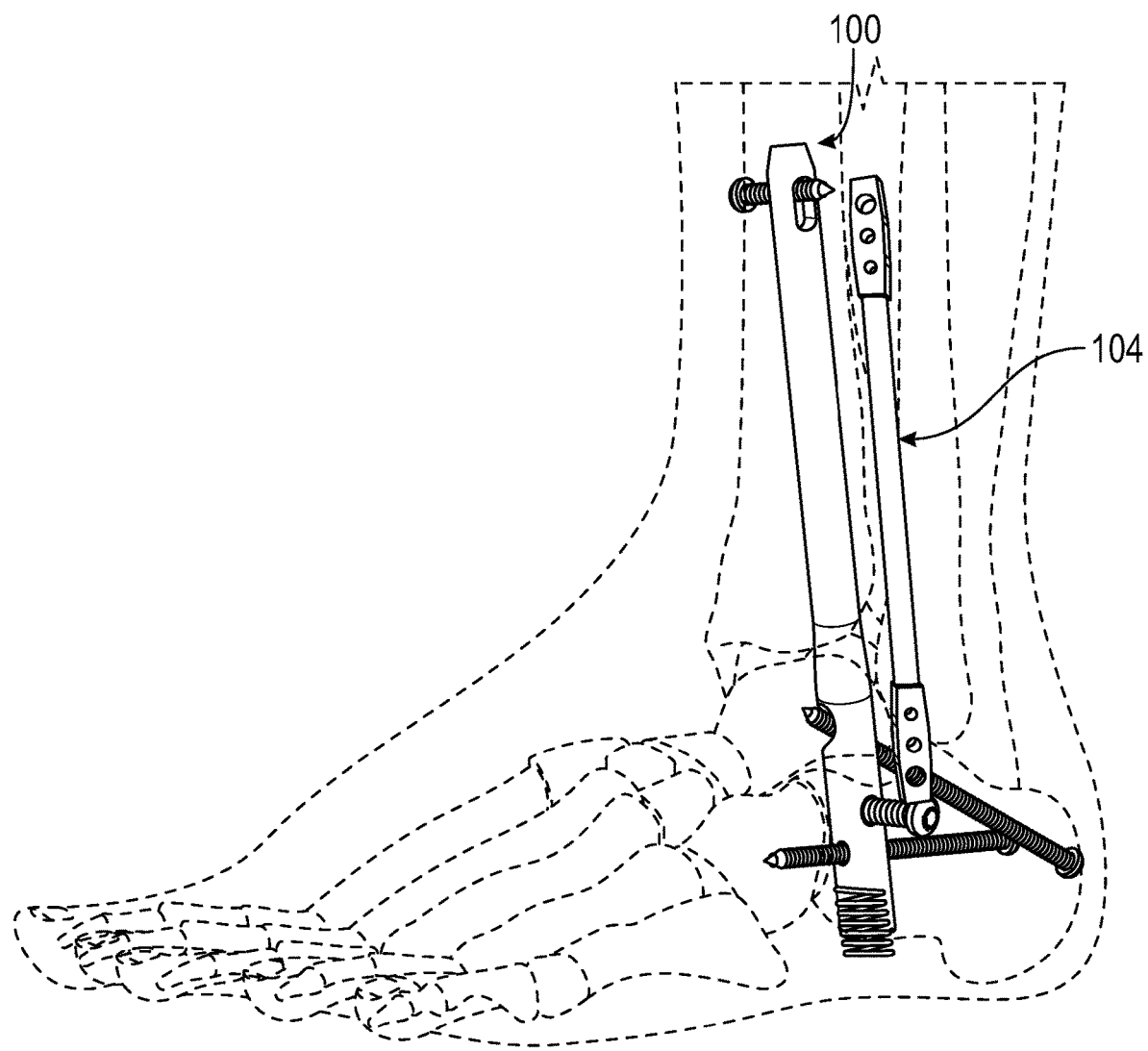
FIG. 10 illustrates a shape memory material connecting member of the arthrodesis device of FIG. 9.

Additional embodiments of this disclosure include the provision and use of arthrodesis devices configured as compression intramedullary (IM) nails, which may be manufactured from Titanium, stainless steel, or the like. Those IM nails may include shape memory materials (e.g., materials capable of exhibiting superelasticity and/or a temperature-induced shape change), which either pull or push locking screws together, and thereby effectively pulling or pushing bone fragments together. It should be appreciated that features of the following examples may also be used with the arthrodesis devices 12 described above FIG. 9 illustrates one such exemplary IM nail 100. In an embodiment, locking screws 102, 103 are interconnected to one another (e.g., inside the bore of the IM nail 100) with a shape memory material connecting member 104, such as a superelastic Nitinol wire, rod (see, e.g., FIG. 10), tube or ribbon. The shape memory material connecting member 104 may be considered to be similar in nature to a tie. Once the proximal locking screw 102 is locked into its round hole 106, the distal locking screw 103 is placed at the bottom or distal end of an oblong dynamic slot 108 that is located furthest from the proximal end. The IM nail 100 may be delivered with the shape memory material connecting member 104 stretched superelastically between the proximal and distal locking screws 102, 103 and is held in the stretched or lengthened condition. Once the locking screws 102, 103 are placed, the shape memory material connecting member 104 is unconstrained and allowed to foreshorten, thus pulling the locking screws 102, 103 together like a tie-rod and effectively pulling the bones together across a fracture site FS. This may reduce the fracture, stabilize the bones, and apply sustained, non-linear compression to the fracture site FS. The shape memory material connecting member 104 may be pre-strained in the IM nail 100 before insertion into the IM space and may be released once in place and the locking screws 102, 103 are cross-threaded into place to secure the IM nail 100.

Throughout this description, the shape memory material of the shape memory material connecting member 52, 104 may be a metal alloy (e.g., Nitinol) or an elastic polymer (e.g., appropriately processed PEEK). The compression IM nail 100 is designed to engage and stabilize bone fragments and to generate compression between the bone fragments. If Nitinol is used, the shape memory material connecting member 104 may be constrained in the "cold" condition. In doing so, this may take considerably less force to strain the non-austenitic form of the shape memory material. The load that is required to stretch martensitic Nitinol may be less than half that required to stress the material in its austenitic phase. It is possible to stretch the Nitinol up to 8% strain along the material's Upper Plateau, unload 2% strain allowing the recoverable force to decrease by almost 50% to the materials Lower Plateau, so when it is finally unconstrained and allowed to recover the balance of the 6% strain it does so on the lower plateau so the force it too great that it damages the interlocking screws 102, 103 or the bone that the screws 102, 103 are inserted into.

Furthermore, the surface finish of the shape memory material connecting member 104 effects its biocompatibility and fatigue life. Prior to straining, the shape memory material connecting member 104 may be passivated to remove embedded surface contaminants that may have resulted from the manufacturing process. Passivation also creates a biocompatible oxide layer on the surface of Nitinol. Straining the Nitinol shape memory material connecting member 104 with a high load (i.e., the type of high load required to stress the Nitinol in an austenitic phase) can damage this biocompatible oxide layer, and can embed particles into its surface. Lower loads (i.e., the type of loads required to stress the compression screw in a non-austenitic phase) will minimize any damage to the surface finish.

With the Nitinol shape memory material connecting member 104 "cold" (i.e., maintained below its austenite start temperature, more preferably below its martensite start temperature, and most preferably below its martensite finish temperature) and strained (i.e., stretched), the shape memory material connecting member 104 is installed to constrain the distal locking screw 103 from shortening and migrating to the proximal end of the oblong dynamic slot 108. More particularly, with the Nitinol shape memory material connecting member 104 maintained below its austenite start temperature, the ends of the stretched Nitinol are threaded to the ends caps of the IM nail 100 to keep the material stretched. The Nitinol shape memory material connecting member 104 can then be warmed above its austenite start temperature and it will not foreshorten due to the presence of threaded ends caps 110 retaining the Nitinol shape memory material connecting member 104 in the stretched, constrained martensite.

However, when the end caps 110 are unthreaded and released, the shape memory material connecting member 104 will attempt to revert back to its non-strained (i.e., unstretched) length, i.e., the Nitinol member will attempt to foreshorten and the compressive force generated by the strained superelastic material which is trying to foreshorten puts sustained compression on the interlocking screws 102, 103, strain in the oblong dynamization slots 108 and put sustained, compressive loads on the fracture site FS.

Note that the Nitinol shape memory material connecting member 104 is configured so that the force that is generated by the material foreshortening is less than the strength of the locking screws 102, 103, so that compression does not bend or break the locking screws 102, 103 when attempting to foreshorten. Additionally the Nitinol shape memory material connecting member 104 is specifically engineered so not to apply too much force to the bones so aggressively that the screws 102, 103 "tear through" the bone tissue. The compressive forces of the shape memory material connecting member 104 can be controlled by modulating the material properties and/or the geometry of the shape memory material connecting member 104.

The percentage of cold work in the shape memory material connecting member 104 can affect the compressive force generated by the device 104. As the percentage of cold work increases, the compression force declines. In an embodiment, the shape memory material connecting member 104 includes between about 15% and 55% cold work to control the recovery force of the Nitinol shape memory material connecting member 104.

Another material property that affects the compression force of the shape memory material connecting member 104 is the temperature differential between the body that the compression screw will be implanted into (assumed to be 37° C., which is the temperature of a human body) and the austenite finish temperature of the shape memory material connecting member 104. A smaller temperature differential between the two will result in the Nitinol shape memory material connecting member 104 generating a small compressive load; conversely, the larger the temperature differential between the two will result in a Nitinol connecting member generating a larger compressive load. In an embodiment, the shape memory material that the shape memory material connecting member 104 is made out of includes an austenite finish temperature of greater than about 10° C. This may result in a temperature differential of less than about 47° C. when the shape memory material connecting member 104 is implanted in a human body.

The geometry of the shape memory material connecting member 104 also affects the compression force that is ultimately generated. The cross-sectional area of the shape memory material connecting member 104 affects the compression force. As the cross-sectional area increases, so does the compression force that the shape memory material connecting member 104 will generate. In this respect, it should be appreciated that it is beneficial for the compression force generated by foreshortening the shape memory material connecting member 104 to be constant as the bone relaxes and remodels. Thus, in an embodiment, the cross-section of the shape memory material connecting member 104 may have a constant cross-section over its entire length. Cross-sections that are not uniform over the length of the shape memory material connecting member 104 can result in an increase or decrease in compression as the shape memory material connecting member 104 shortens.

In another embodiment, the shape memory material connecting member 104 is stretched while it is at a temperature below its austenite start temperature, and with the end caps 110 threading the shape memory material connecting member 104 in the stretched condition, below its austenite start temperature. However, if desired, the shape memory material connecting member 104 may be stretched while it is at a temperature above its austenite start temperature, whereby to create stress-induced martensite.

In another embodiment, the shape memory material connecting member 104 of the IM nail 100 is cannulated and provided in the form of a sterilized kit. The kit may include additional instruments to aid in the implantation of the IM nail 100 (e.g., k-wire, drill bit, screw size guide, etc.).

TTC ankle fusion is a technique that may be used to achieve functional, stable, and pain-free orthopedic fusion for the treatment of appropriate medical conditions. Intentional bone fusions which are often unsuccessful can lead to patient pain, recurring surgery, infection, loss of limb function, and/or, in extreme cases, limb amputation. IM nails that can provide sustained compressive forces across a bone fusion site despite bone resorption processes are desired. By connecting and pulling the locking screws 102, 103 together, the IM nail 100 may provide sustained, compression to the fracture site.

Figure 11:
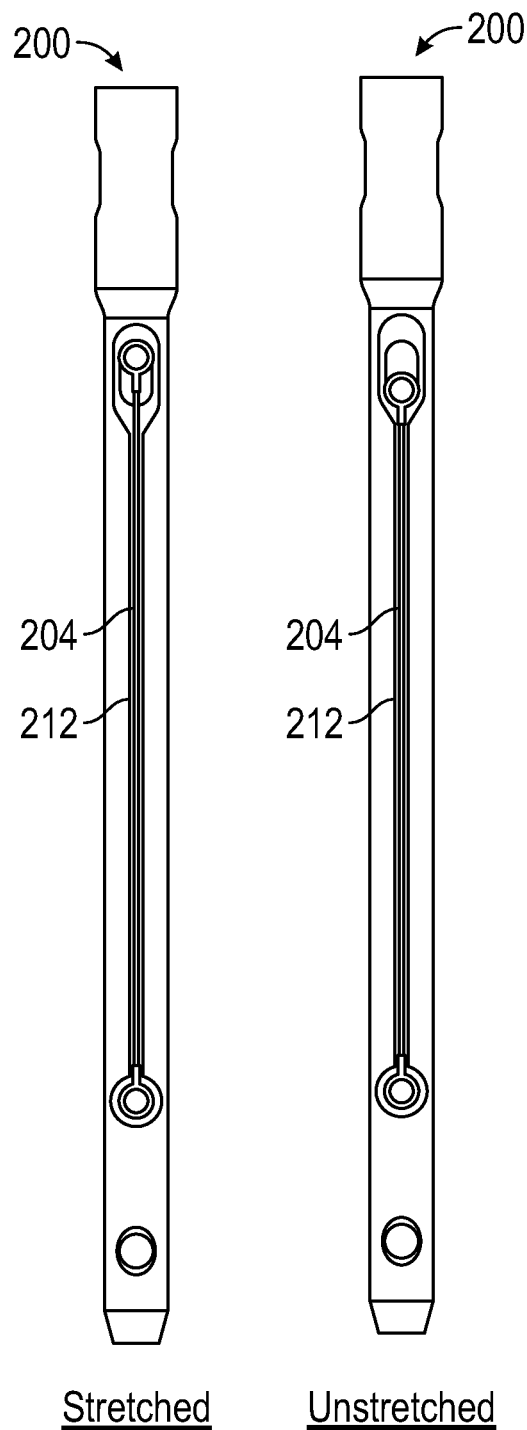
FIG. 11 illustrates stretched and unstretched conditions of a shape memory material connecting member of an arthrodesis device.
Figure 12:
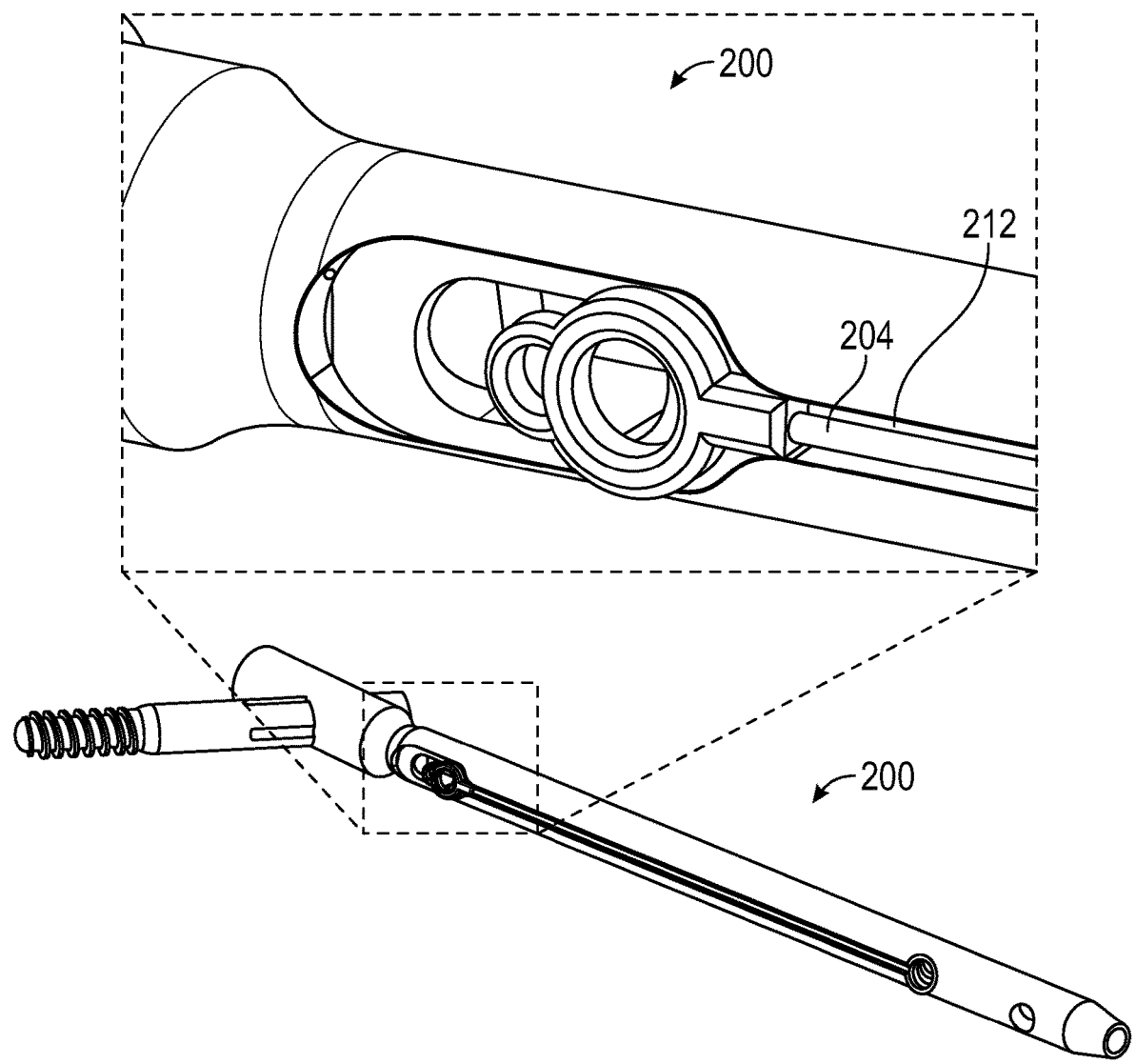
FIG. 12 illustrates a channel for receiving the shape memory material connecting member of FIG. 11.

FIGS. 11 and 12 illustrate another exemplary IM nail 200. The IM nail 200 includes a shape memory material connecting member 204 that can be located on the outside of the IM nail 200 (see FIG. 11), or could include a combination of both outer and inner shape memory material connecting members 204. The shape memory material connecting member 204 can be recessed into a channel 212 (e.g., a milled channel) or flute in the outer diameter of the IM nail 200. In such an embodiment, the shape memory material connecting member 204 may not sit proud of the diameter (see, e.g., FIG. 12).

Figure 13:
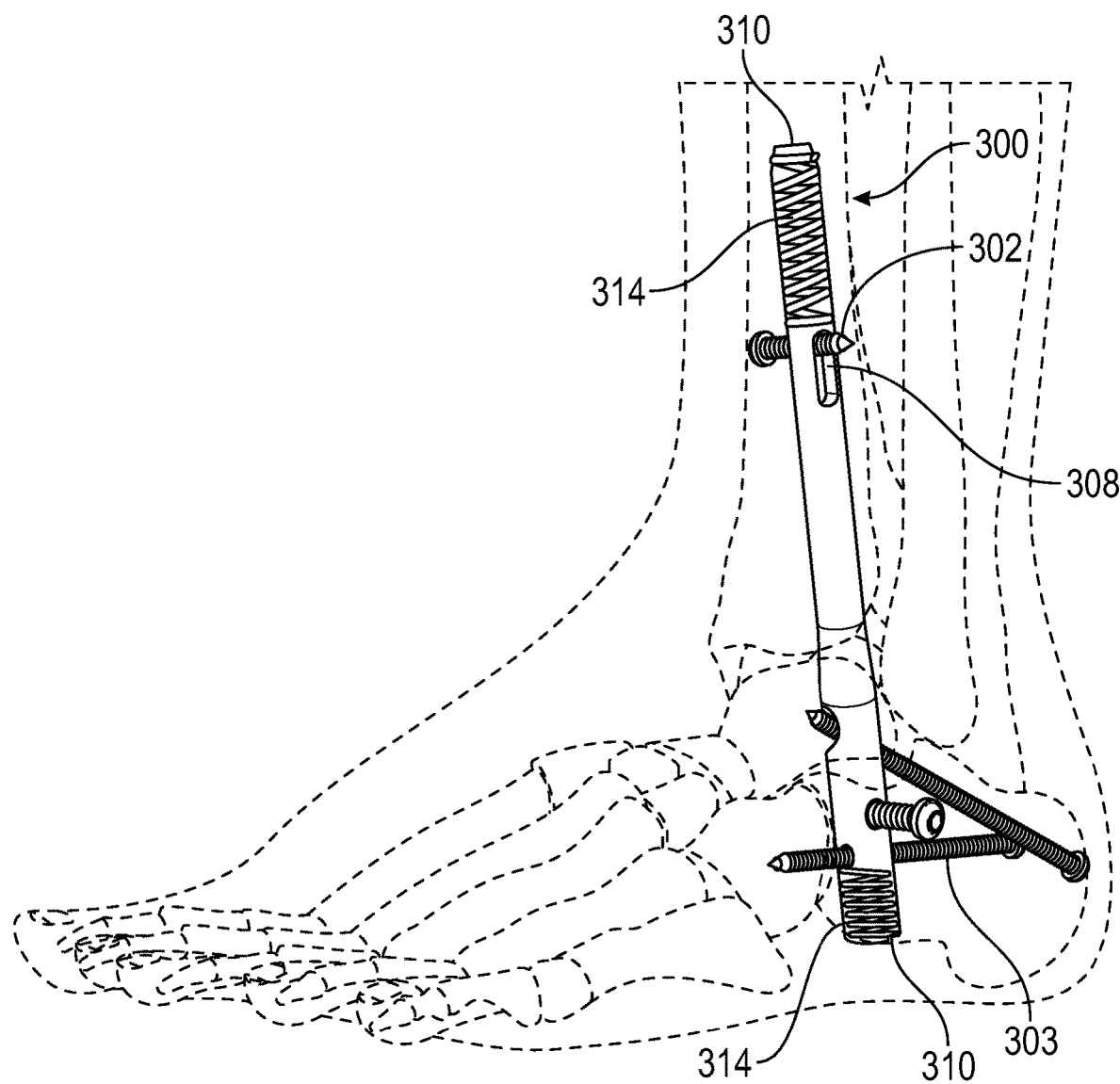
FIG. 13 illustrates another exemplary arthrodesis device.

FIG. 13 illustrates another exemplary IM Nail 300. In an embodiment, interconnecting locking screws 302, 303 can be forced together by using one or more springs 314. The springs 314 can be made of various materials, including but not limited to, stainless steel, Titanium, cobalt-chrome, MP35N, Nitinol, L605, and various other biocompatible alloys.

There can be one or multiple springs 314 used to push the interconnecting locking screws 302, 303 together so long as there is at least one slot for the screw to axially travel in. In an embodiment, the screw 302 that is being pushed along its slot 308 is applying sustained compression to a fracture site. The springs 314 can be positioned between end caps 310 of the IM nail 300 and the locking screws 302, 303 so that the springs 314 push the locking screws 302, 303 toward a fracture site. Alternatively, the springs 314 can be part of a set-screw positioned just distal the end cap but proximal to the interconnecting locking screw 302 in the dynamization slot 308. It is possible to use a coil spring, wave spring, or die set spring; or a combination thereof. The spring 314 can be made of MP35N, Titanium alloys, Elgiloy, Cobalt Chrome alloys, and various other biocompatible alloys.

Figure 14:
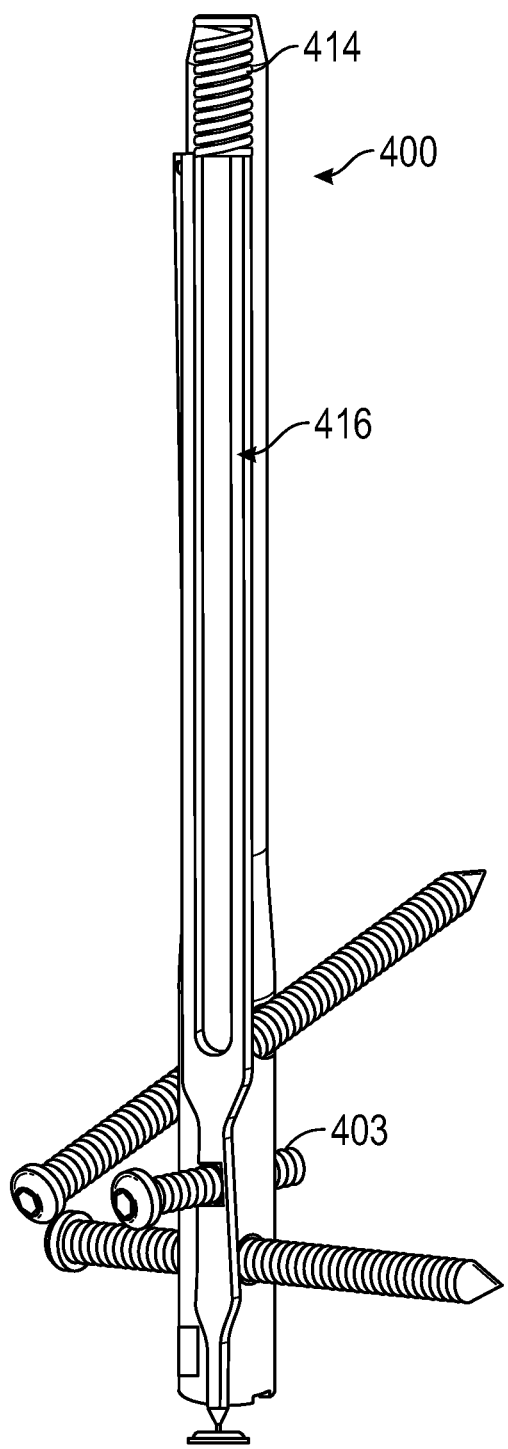
FIG. 14 illustrates another exemplary arthrodesis device, shown both before and during the application of dynamic compression.
Figure 14:
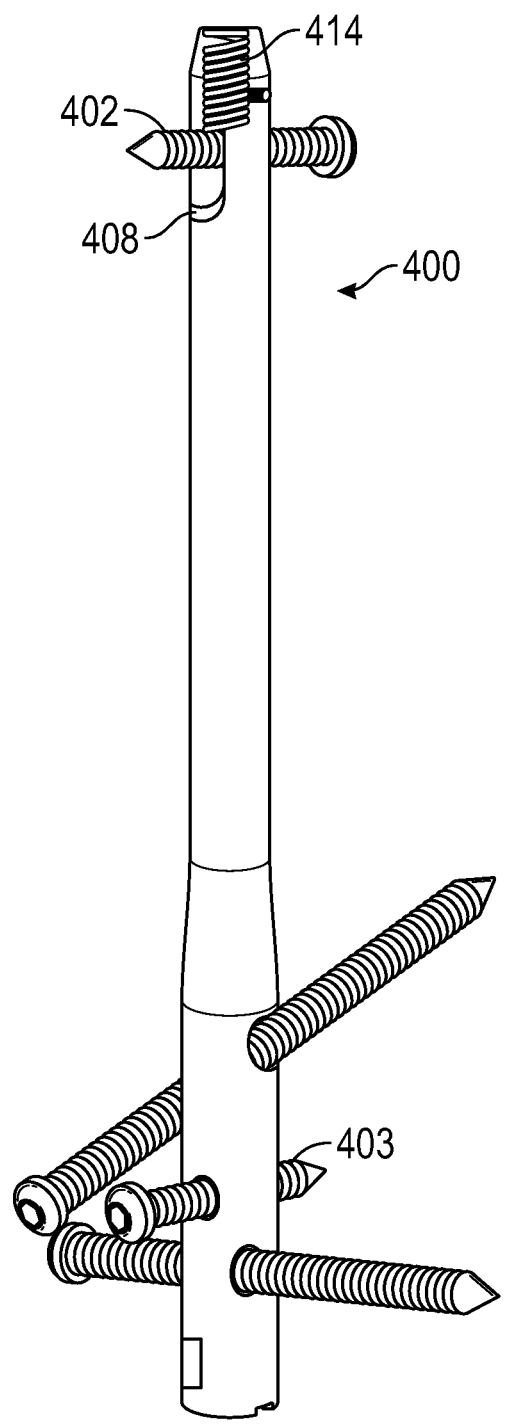

FIG. 14 illustrates yet another exemplary IM nail 400. The IM nail 400 may be a TTC fusion nail having a spring 414 and a tuning fork device 416 which can be inserted into the IM nail 400 to push or compress the spring 414, thus allowing access or passage of the interconnecting locking screws 402, 403 thru the IM nail 400. Once the interconnecting screws 402, 403 are threaded in place, the tuning fork device 416 may be removed by pulling out the open end. The spring 414 may then be allowed to expand and apply a force against the screw 402 in the dynamization slot 408.

Figure 15:
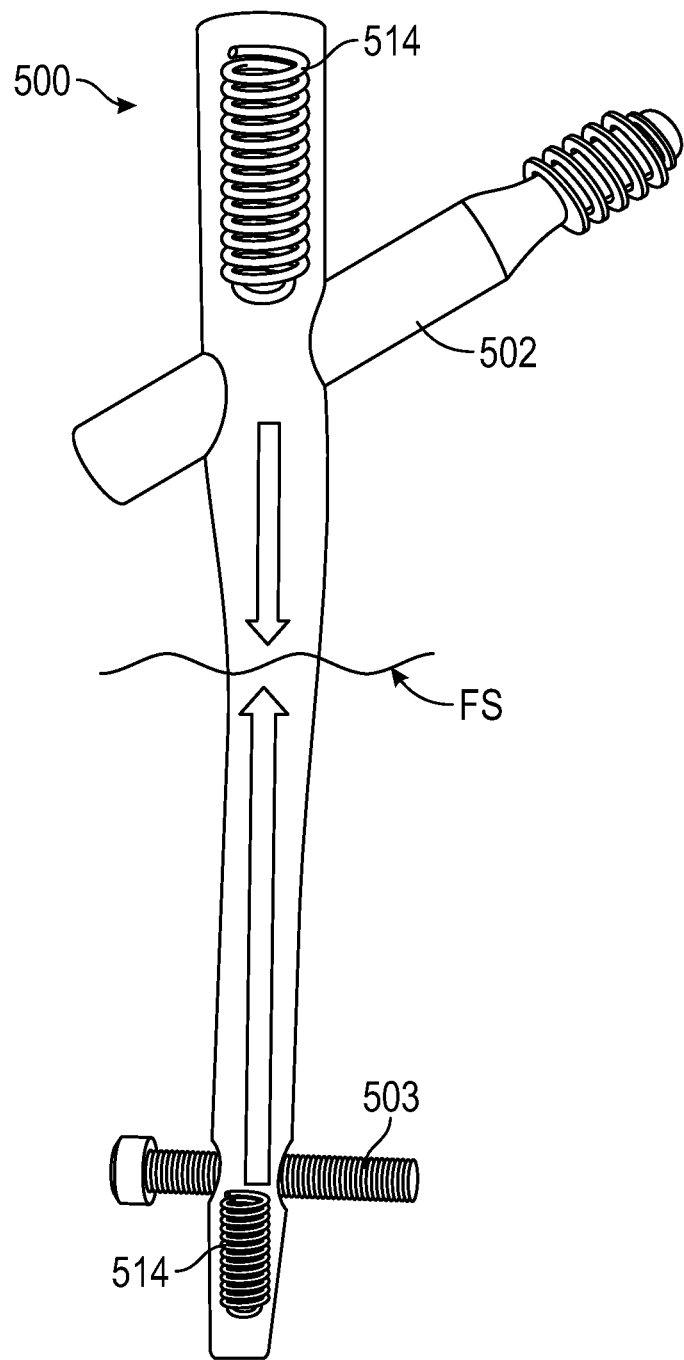
FIG. 15 illustrates yet another exemplary arthrodesis device.

FIG. 15 illustrates yet another IM nail 500, which may be a Cephalomedullary IM nail, for example. In this embodiment, springs 514 apply compression to interconnecting screws 502, 503 to create sustained compression. The springs 514 can compress against the screws 502, 503 themselves, or may compress against a device that cradles or nests the screws 502, 503.

Figure 16:
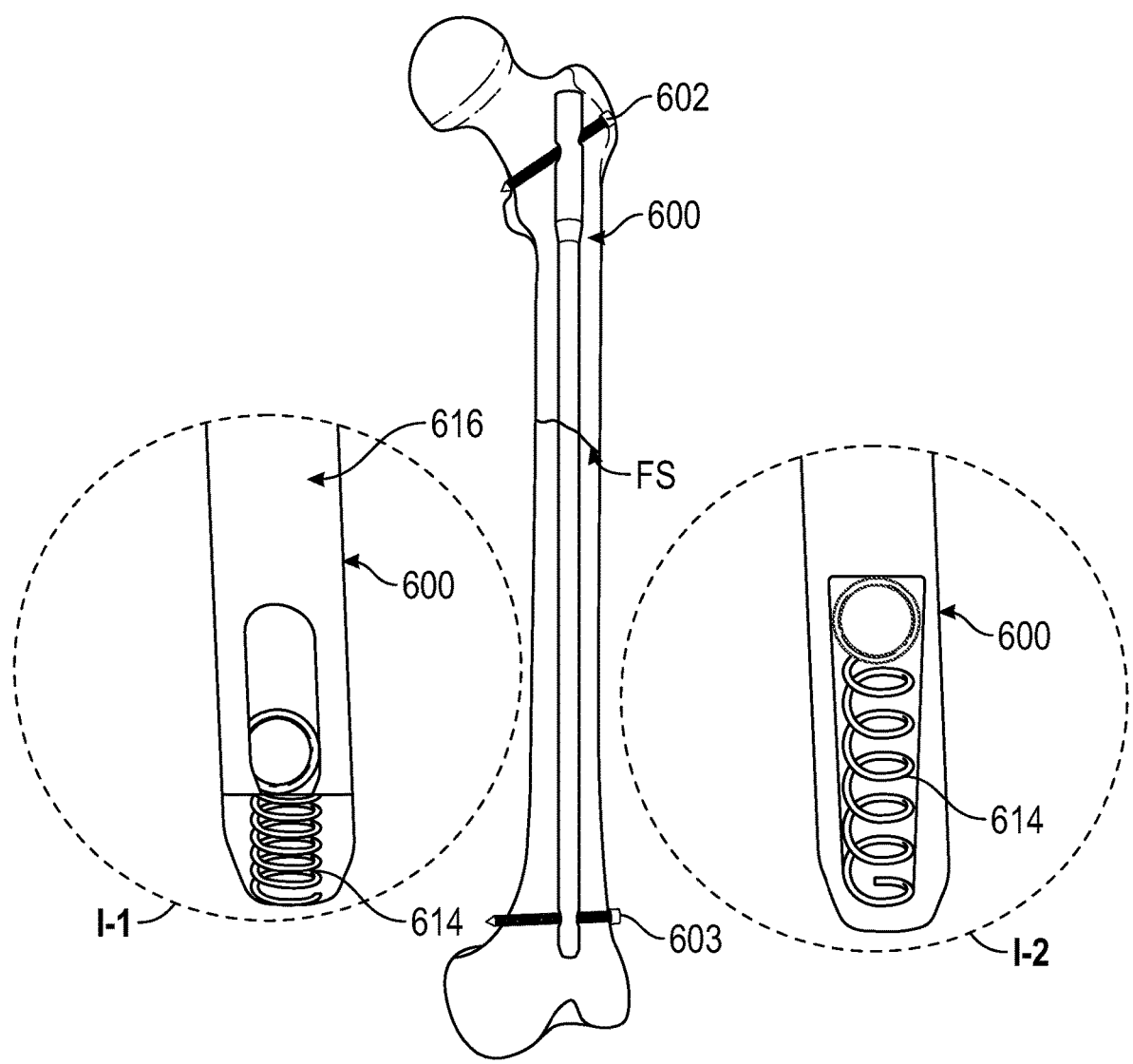
FIG. 16 illustrates another exemplary arthrodesis device.
Figure 17:
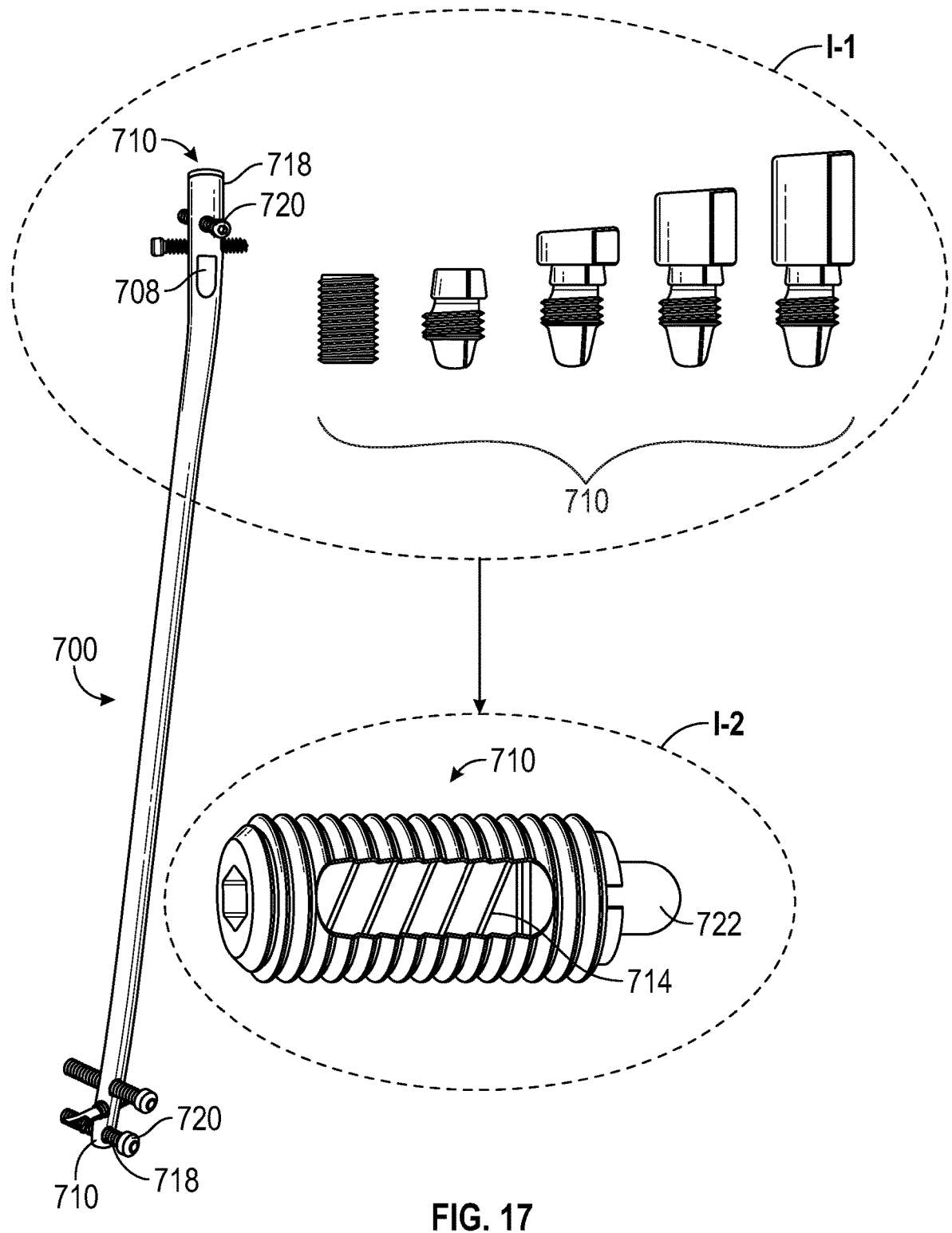
FIG. 17 illustrates another exemplary arthrodesis device.

FIG. 16 illustrates another IM nail 600. The IM nail 600 may include a tuning fork device 616 that compresses a spring 614 allowing passage of a screw 602, 603 through the IM nail 600 (see inset I-1). The tuning fork device 616 may be released off the spring 614 to expand the spring 614 (see inset I-2), thus pushing the IM nail 600 proximally and loading the fracture site FS.

FIGS. 17-21 illustrate yet another exemplary IM nail 700. The IM nail 700 may include end caps 710 that thread into openings 718 of the IM nail 700. The end caps 710 may be static and may thread against a static set-screw 720. A spring 714 may be positioned within the end cap 710 (see inset I-2), thus rendering it dynamic. The end cap 710 can be threaded and designed to look more like a spring plunger. The end cap 710 can include an internal thread which pushes a plunger 722 against an interconnecting screw 702 that may be placed through an oblong, dynamization slot 708 (see FIG. 17).

Figure 18:
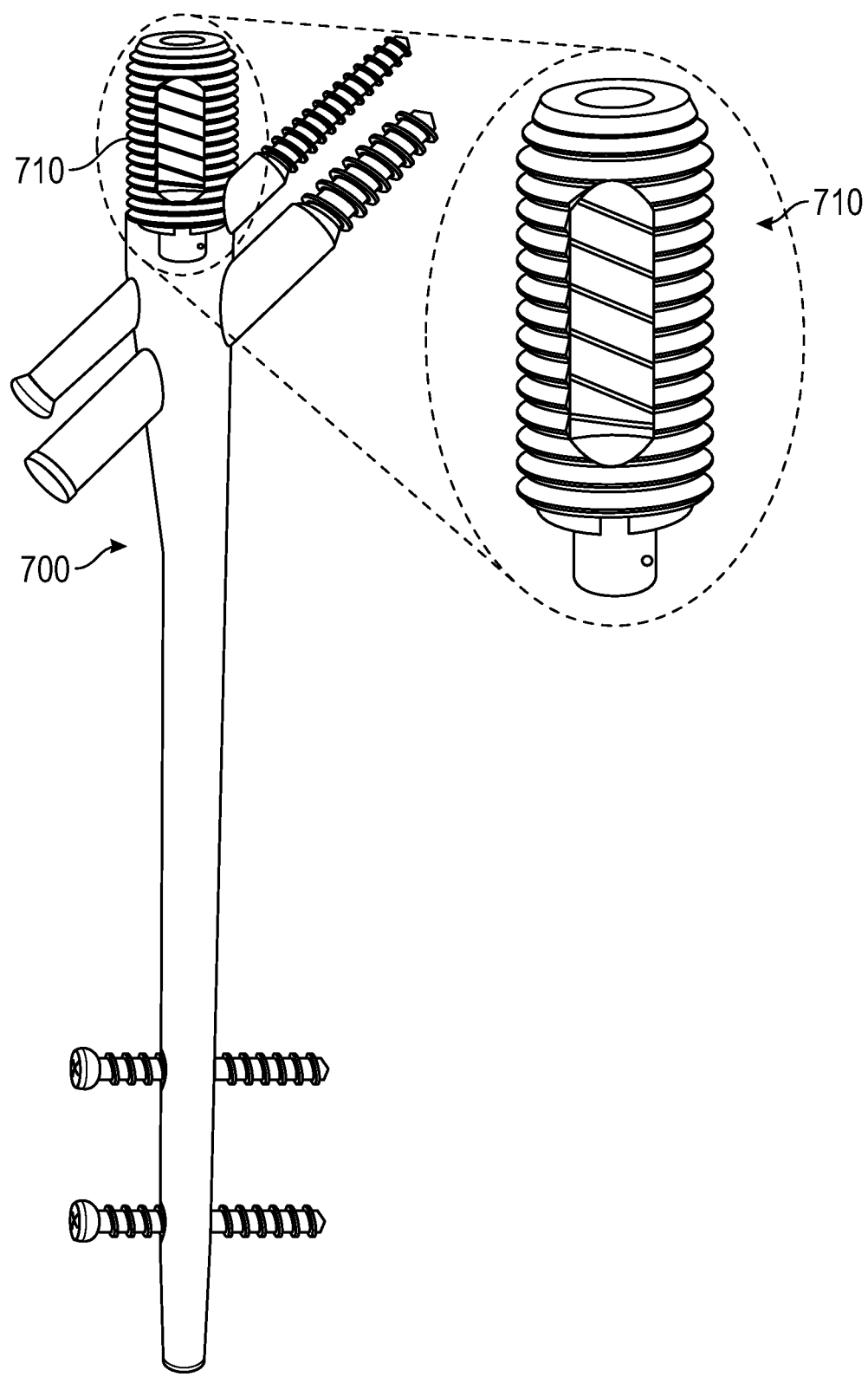
FIG. 18 illustrates another exemplary arthrodesis device.
Figure 19:
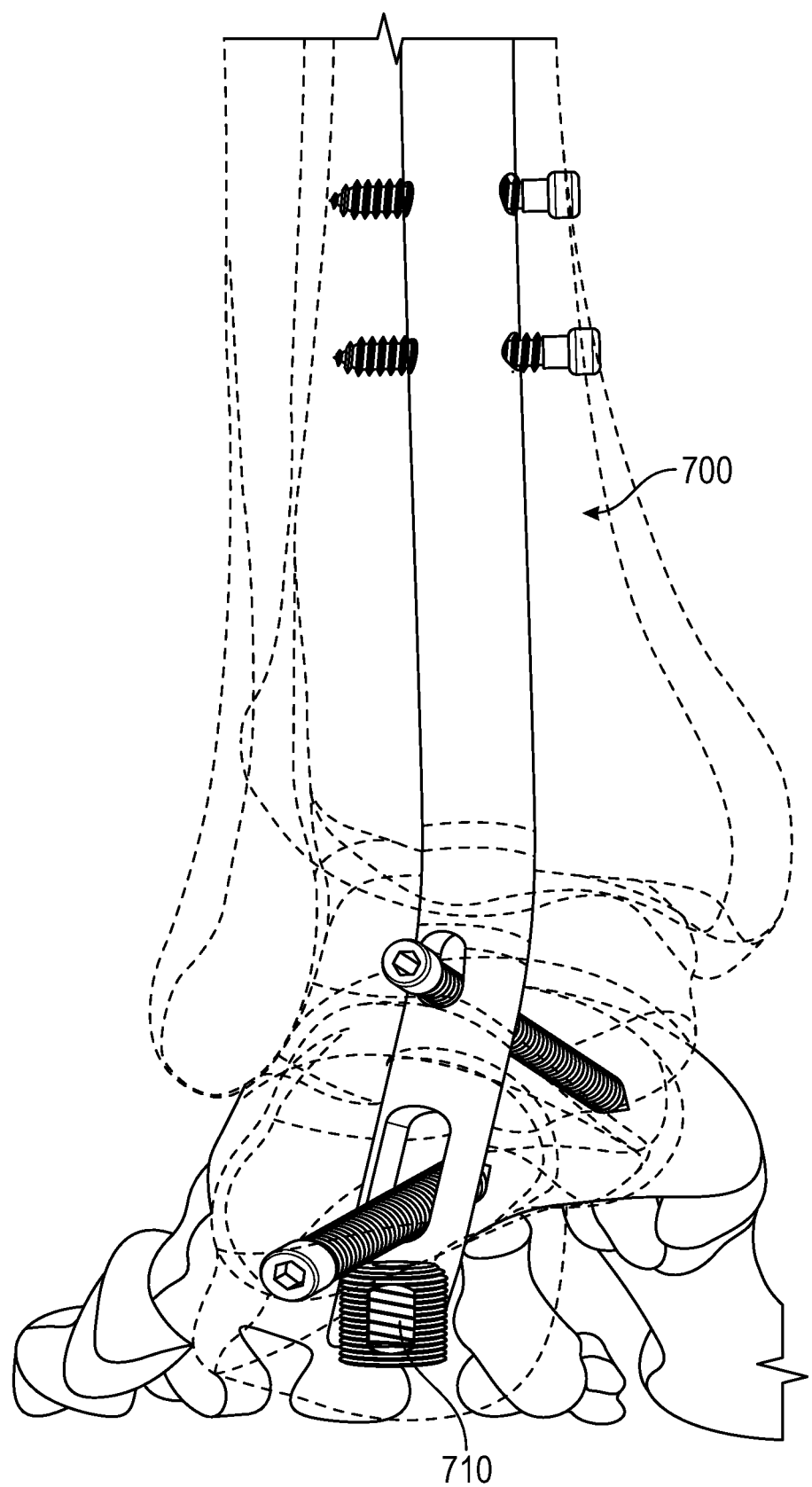
FIG. 19 illustrates yet another exemplary arthrodesis device.
Figure 20:
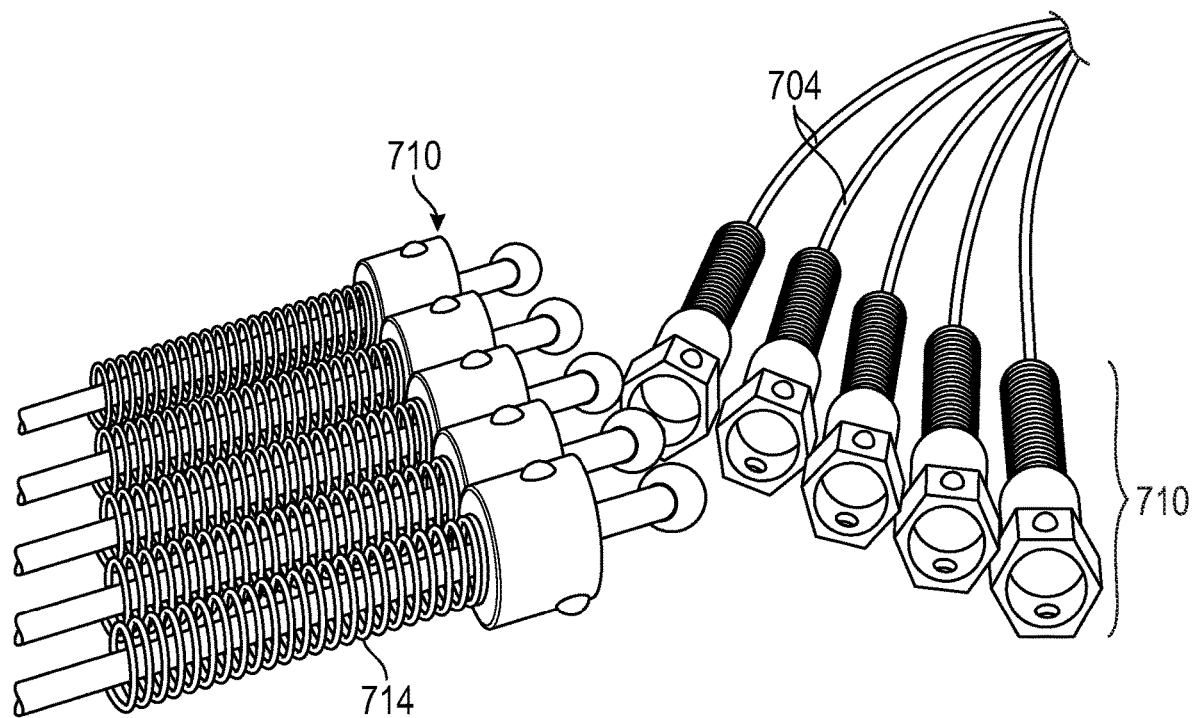
FIG. 20 illustrates exemplary end caps for an arthrodesis device.
Figure 21:
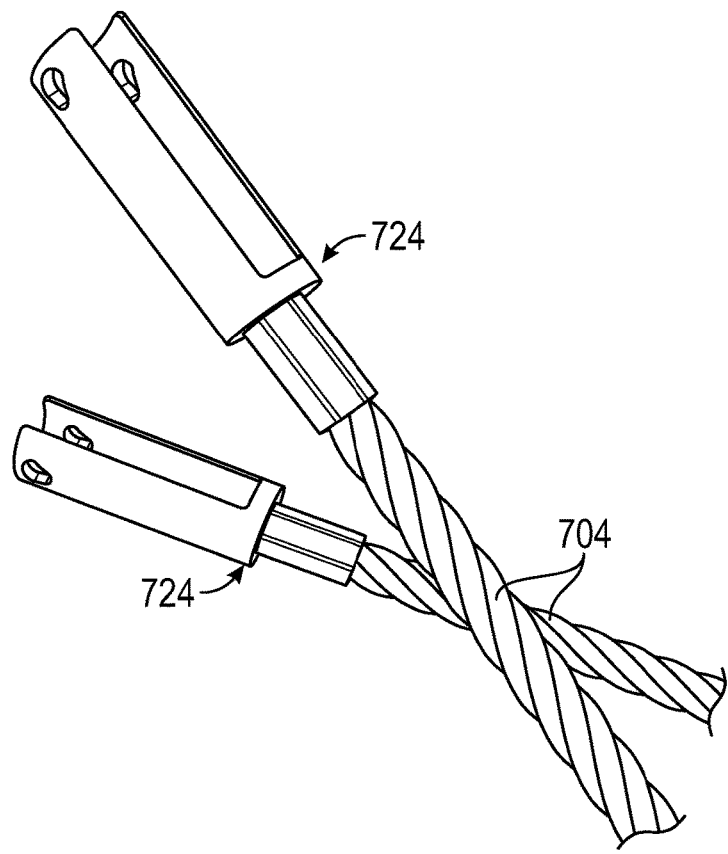
FIG. 21 illustrates additional exemplary end caps for an arthrodesis device.

The dynamic end caps 710 can be used in all types of IM nails and such arthrodesis devices. FIG. 18 illustrates their use in a femoral nail, and FIG. 19 illustrates their use for an ankle nail.

It is also possible to pull the screws 702, 703 together with a Nitinol connecting member 704 while also using springs 714 to push the interconnecting locking screws 702, 703 together. This may maximize the sustained compression (see, e.g., FIG. 20). The connecting member 704 can be a wire or cable with welded bead ends or swaged end fittings 724 (see, e.g., FIG. 21). The end caps 710 can accept a compression screw or spring and can be swaged or welded to the connecting member 704.

This disclosure provides novel arthrodesis devices capable of bringing bone or bone fragments into close proximity with each other, generating a compressive load, and maintaining the compressive load for a prolonged period of time while healing occurs.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An arthrodesis device, comprising:
a sleeve extending along a longitudinal axis between a proximal portion and a distal portion;
a proximal body located inside the proximal portion;
a distal body located inside the distal portion;
a shape memory material connecting member connected to both the proximal body and the distal body; and
a tensioning device connected to the proximal body or the distal body,
wherein the tensioning device is tensionable to move the proximal body or the distal body inside the sleeve,
wherein at least one of the proximal body or the distal body is a separate and distinct component from the shape memory material connecting member.

2. The device as recited in claim 1, wherein the sleeve includes at least one opening configured to receive a fixation device.

3. The device as recited in claim 1, wherein a first opening is located within the proximal portion of the sleeve and receives a tibial screw, a second opening is located within the distal portion of the sleeve and receives a talar screw, and a third opening is located within the distal portion of the sleeve and receives a calcaneal screw.

4. The device as recited in claim 1, wherein the shape memory material connecting member is a rod made of Nitinol (NiTi).

5. The device as recited in claim 1, wherein the shape memory material connecting member includes an elongated shaft extending between a first threaded portion and a second threaded portion.

6. The device as recited in claim 1, wherein the shape memory material connecting member is configured to move between an unstretched position and a stretched position to generate a compressive force across bones of a joint.

7. The device as recited in claim 1, wherein the tensioning device is a cable received through a non-threaded opening of the distal body.

8. The device as recited in claim 1, wherein the proximal body includes a first length and the distal body includes a second length that is greater than the first length.

9. The device as recited in claim 1, wherein the sleeve, the proximal body, and the distal body are each comprised of a titanium alloy.

10. The device as recited in claim 1, comprising a first screw received through the proximal portion of the sleeve, a second screw received through the distal portion of the sleeve, and a third screw received through the distal portion of the sleeve.

11. A method of performing an arthrodesis procedure, comprising:
   inserting an arthrodesis device within a joint;
   inserting a first fixation device through the arthrodesis device;
   inserting a second fixation device through the arthrodesis device;
   tensioning a tensioning device of the arthrodesis device, wherein tensioning the tensioning device stretches a shape memory material connecting member of the arthrodesis device from an unstretched condition to a stretched condition,
   wherein the shape memory material connecting member is removably connected to a proximal body and a distal body at a location inside the arthrodesis device; and
   releasing tension on the tensioning device,
   wherein releasing the tension on the tensioning device causes the shape memory material connecting member to move back toward the unstretched condition, thereby applying a compressive load across bones of the joint.

12. The method as recited in claim 11, wherein the joint is a tibio-talo-calcaneal (TTC) joint of an ankle.

13. The method as recited in claim 11, comprising, prior to inserting the arthrodesis device:
   inserting a guide wire into the joint; and
   reaming a passage through the joint for accommodating the arthrodesis device.

14. The method as recited in claim 11, wherein the first fixation device is calcaneal screw and the second fixation device is a tibial screw.

15. The method as recited in claim 14, comprising:
   inserting a third fixation device through the arthrodesis device after inserting the second fixation device, wherein the third fixation device is either a talar screw or a calcaneal screw.

16. The method as recited in claim 11, wherein the tensioning device is connected to the distal body, wherein tensioning the tensioning device includes:
   translating the distal body in a proximal to distal direction relative to the joint.

17. The method as recited in claim 16, wherein translating the distal body moves the shape memory material connecting member of the arthrodesis device from the unstretched condition to the stretched condition, and further wherein the proximal body is fixed from movement prior to tensioning the tensioning device.

18. The method as recited in claim 17, wherein inserting a third fixation device substantially locks a positioning of the distal body.

19. The method as recited in claim 11, wherein the tensioning device is a metallic cable.

20. An arthrodesis device, comprising:
   a sleeve extending along a longitudinal axis between a proximal portion and a distal portion;
   a proximal body located inside the proximal portion;
   a distal body located inside the distal portion;
   a Nitinol rod removably connected to both the proximal body and the distal body; and
   a tensioning device connected to the proximal body or the distal body,
   wherein the tensioning device is tensionable to move the proximal body or the distal body distally inside the sleeve, thereby stretching the Nitinol rod,
   wherein the Nitinol rod is a separate and distinct component from either the proximal body or the distal body,
   wherein the proximal body and the distal body are comprised of a different material than the Nitinol rod.

* * * * *